(12) United States Patent
Annunziata et al.

(10) Patent No.: US 9,406,872 B1
(45) Date of Patent: Aug. 2, 2016

(54) FABRICATING TWO-DIMENSIONAL ARRAY OF FOUR-TERMINAL THIN FILM DEVICES WITH SURFACE-SENSITIVE CONDUCTOR LAYER

(71) Applicant: International Business Machines Corporation, Armonk, NY (US)

(72) Inventors: Anthony J. Annunziata, Stamford, CT (US); Ching-Tzu Chen, Ossining, NY (US); Joel D. Chudow, Bronx, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/941,878

(22) Filed: Nov. 16, 2015

(51) Int. Cl.
    *H01L 43/06*     (2006.01)
    *G01N 27/12*     (2006.01)
    *H01L 43/04*     (2006.01)
    *H01L 43/14*     (2006.01)

(52) U.S. Cl.
    CPC ............ *H01L 43/065* (2013.01); *G01N 27/125* (2013.01); *H01L 43/04* (2013.01); *H01L 43/14* (2013.01)

(58) Field of Classification Search
None
See application file for complete search history.

(56) References Cited

U.S. PATENT DOCUMENTS

| | | | |
|---|---|---|---|
| 7,361,991 B2 | 4/2008 | Saenger et al. | |
| 7,902,820 B2 | 3/2011 | Vervaeke et al. | |
| 7,943,480 B2 | 5/2011 | Edelstein et al. | |
| 8,062,497 B2 | 11/2011 | Witvrouw et al. | |
| 8,304,906 B2 | 11/2012 | Huang et al. | |
| 8,404,582 B2 | 3/2013 | Horak et al. | |
| 8,592,876 B2 | 11/2013 | Ding et al. | |
| 2009/0014885 A1* | 1/2009 | Chen | ........................ H01L 45/06 257/774 |
| 2012/0112152 A1* | 5/2012 | Bulovic | .................. H01L 45/00 257/2 |
| 2012/0231604 A1 | 9/2012 | Liu | |
| 2013/0214415 A1 | 8/2013 | Pachamuthu et al. | |
| 2014/0008611 A1* | 1/2014 | Geim | .................. H01L 29/1606 257/14 |
| 2014/0145735 A1* | 5/2014 | Koester | ................ G01N 27/227 324/686 |
| 2014/0197459 A1* | 7/2014 | Kis | .................... H01L 29/66742 257/194 |
| 2015/0323482 A1* | 11/2015 | Shimoyama | ........ G01N 27/4146 73/31.06 |
| 2015/0364614 A1* | 12/2015 | Withers | ................. H01L 31/028 257/26 |

OTHER PUBLICATIONS

A. J. Annunziata et al., "Thin Film Device With Protective Layer," U.S. Appl. No. 14/571,771, filed Dec. 16, 2014.
C.-T. Chen et al., "Low-damage high-throughput grazing-angle sputter deposition on graphene," Applied Physics Letters, vol. 103, No. 3, Jul. 16, 2013, pp. 1-25.
List of IBM Patents or Patent Applications Treated as Related; Date Filed: Nov. 16, 2015; 2 pages.

* cited by examiner

*Primary Examiner* — Michael Jung
(74) *Attorney, Agent, or Firm* — Cantor Colburn LLP; Vazken Alexanian

(57) ABSTRACT

A technique relates to a semiconductor device. First metal contacts are formed on top of a substrate. The first metal contacts are arranged in a first direction, and the first metal contacts are arranged such that areas of the substrate remain exposed. Insulator pads are positioned at predefined locations on top of the first metal contacts, such that the insulator pads are spaced from one another. Second metal contacts are formed on top of the insulator pads, such that the second metal contacts are arranged in a second direction different from the first direction. The first and second metal contacts sandwich the insulator pads at the predefined locations. Surface-sensitive conductive channels are formed to contact the first metal contacts and the second metal contacts. Four-terminal devices are defined by the surface-sensitive conductive channels contacting a pair of the first metal contacts and contacting a pair of the metal contacts.

10 Claims, 10 Drawing Sheets

US 9,406,872 B1

FABRICATING TWO-DIMENSIONAL ARRAY OF FOUR-TERMINAL THIN FILM DEVICES WITH SURFACE-SENSITIVE CONDUCTOR LAYER

BACKGROUND

The present invention relates generally to the field of semiconductor devices, and more specifically, to fabrication of a two-dimensional array of four-terminal thin film devices.

A topological insulator is a material with time reversal symmetry and non-trivial topological order that behaves as an insulator in its interior but whose surface contains conducting states, meaning that electrons can only move along the surface of the material.

A thin film is a layer of material ranging from fractions of a nanometer (monolayer) to several micrometers in thickness. Electronic semiconductor devices are a main application benefiting from thin-film construction.

SUMMARY

According to one embodiment, a method of fabricating a semiconductor device is provided. The method includes forming a first plurality of metal contacts on top of a substrate, where the first plurality of metal contacts are arranged in a first direction, and where the first plurality of metal contacts are arranged such that areas of the substrate remain exposed. The method includes forming insulator pads at predefined locations on top of the first plurality of metal contacts, such that the insulator pads are spaced from one another, and forming a second plurality of metal contacts on top of the insulator pads, such that the second plurality of metal contacts are arranged in a second direction different from the first direction. The first and second plurality of metal contacts sandwich the insulator pads at the predefined locations. Also, the method includes depositing a surface-sensitive conductive layer on top of the first plurality of metal contacts, the second plurality of metal contacts, the insulator pads, and the substrate, and etching the surface-sensitive conductive layer to leave a plurality of conductive channels. The etching includes removing the surface-sensitive conductive layer from the insulator pads and removing the surface-sensitive conductive layer from the first and second plurality of metal contacts at the predefined locations. Four-terminal devices are defined by the plurality of conductive channels contacting a pair of the first plurality of metal contacts and contacting a pair of the second plurality of metal contacts.

According to one embodiment, a semiconductor device is provided. The semiconductor device includes a first plurality of metal contacts on top of a substrate, the first plurality of metal contacts being arranged in a first direction, where the first plurality of metal contacts are arranged such that areas of the substrate remain exposed. The semiconductor device includes insulator pads positioned at predefined locations on top of the first plurality of metal contacts, such that the insulator pads are spaced from one another, and a second plurality of metal contacts on top of the insulator pads, such that the second plurality of metal contacts are arranged in a second direction different from the first direction. The first and second plurality of metal contacts sandwich the insulator pads at the predefined locations. Also, the semiconductor device includes a plurality of surface-sensitive conductive channels contacting the first plurality of metal contacts and the second plurality of metal contacts. Four-terminal devices are defined by the plurality of surface-sensitive conductive channels contacting a pair of the first plurality of metal contacts and contacting a pair of the second plurality of metal contacts.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

DETAILED DESCRIPTION

Embodiments recognize that device technologies based on ultra-thin films (e.g., graphene transistors or sensors, superconducting nanowire signal photon detectors, topological insulator materials used for sensors or logic devices) can be extremely sensitive to operating environments. Embodiments recognize that electrical transport and/or detection can occur at or near the surface of a thin film, or within a thin film thickness, and that damage to the surface of such a thin film, or other effects from environmental exposure, can dramatically impact performance of a device. Further, embodiments recognize that electrical contact is often needed at the edge or underneath a thin film layer within a device. Embodiments describe structures and methods for creating four-terminal protected devices.

Advances in the synthesis of ultra-thin, quasi-two-dimensional (2D) materials such as graphene, quasi-2D semiconductor $MoS_2$, and topological insulators enable unique applications in optoelectronics, electronics, plasmonics, spintronics, and nanoelectromechanical systems (NEMS). These materials, however, are susceptible to performance degradation caused by surface oxidation and adsorbed impurities, rendering applications in ambient environment difficult.

Existing methods for protecting the devices usually involve depositing a dielectric cap or removing a sacrificial layer on top of the active region to form a vacuum cap. The process of depositing a dielectric cap produces trapped charges at the interface, resulting in unintentional doping of the active regions, causing undesirable hysteresis and low-frequency (2-level system) telegraph noise in the devices. Removing a sacrificial layer on top of the active region exposes the active region to further chemical contaminations or physical bombardment after forming the device channel, which also results in unintentional doping, chemical instability, and performance degradation.

Figure 1:
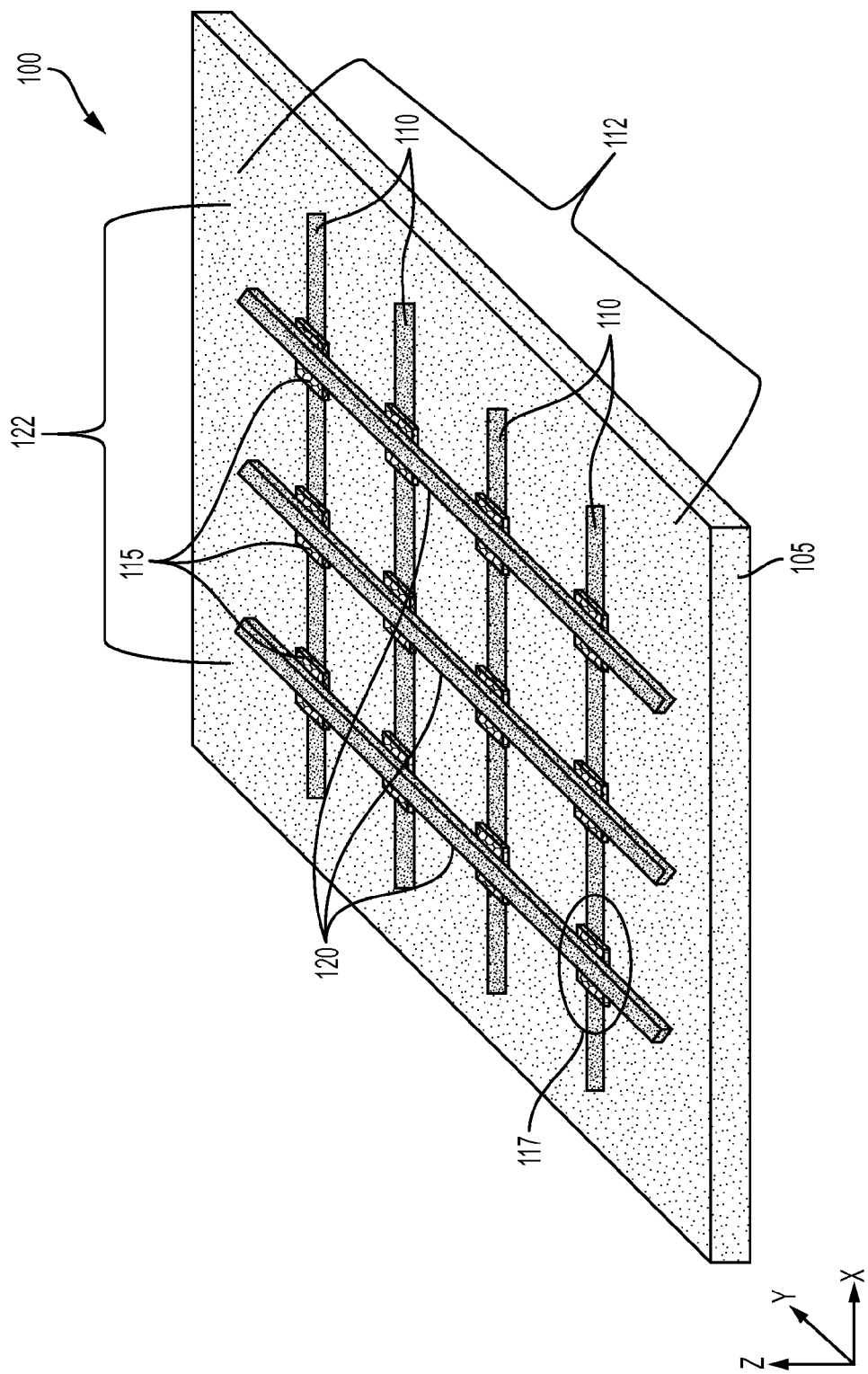
FIG. 1 is a schematic of an intermediate device illustrating insulator pads sandwiched by two metal-rib arrays according to an embodiment.

FIG. 1 is a schematic of an intermediate device 100 illustrating insulator pads sandwiched by two metal-rib arrays 112 and 122 according to an embodiment.

To form the intermediate device 100, a first layer of conductive material may be disposed on top of a non-conducting substrate 105 using techniques understood by one skilled in the art. Examples of the non-conducting substrate 105 may include silicon (Si), germanium, etc. In one implementation, the silicon containing materials may include single crystal Si, polycrystalline Si, silicon-germanium (SiGe), single crystal SiGe, polycrystalline SiGe, amorphous Si, and combinations and multi-layers thereof.

The first layer of conductive material may be etched into a first layer of metal-rib contacts 110 formed on the non-conducting substrate 105 along one direction, such that a first metal-rib array 112 is formed. In one implementation, the first layer of metal-rib contacts 110 may be formed as lines along the x-axis. In one implementation, the first metal-rib contacts 110 may be formed using photolithographic and subtractive etching processes to define the structure of the first metal-rib array 112. Photolithography is a process to pattern parts of a thin film or the bulk of a substrate.

A thin film insulator may be disposed on top of the first layer of metal-rib contacts 110 (as well as the non-conducting substrate 105) using techniques understood by one skilled in the art. The thin film insulator may be etched into thin insulating pads 115 such that the thin insulating pads 115 remain at predefined locations 117 on top of the first layer of metal-rib contacts 110, while other material of the thins film insulator is etched away. In an implementation, the thin film insulator layer may be etched into the thin film insulating pads 115 using photolithography. Examples of the insulating material for the thin film insulating pads 115 may include oxides, nitrides, etc.

A second layer of conductive material may be disposed on top of the thin insulating pads 115 (as well as the first layer of metal-rib contacts 110 and non-conducting substrate 105). The second layer of conductive material may be etched into a second layer of metal-rib contacts 120 formed on the thin insulating pads 115 along another direction, such that a second metal-rib array 122 is formed. The second metal-rib contacts 120 are formed to intersect the first metal-rib contacts 110 at the predefined locations. The second layer of metal-rib contacts 120 is formed on top of the first metal-rib array 112 along another direction, with the thin insulating pads 115 underneath to prevent interlayer shorting. In one implementation, the second layer of metal-rib contacts 120 may be formed as lines along the y-axis. The second metal-rib contacts 120 may be formed using photolithography. As one example, the photolithography process for each layer aligned corresponds to an alignment marking pattern located in the substrate periphery.

Various metals may be utilized as the first and second layers of metal-rib contacts 110 and 120. Examples of the conductive material used for the first and second layers of metal-rib contacts 110 and 120 may include copper, aluminum, gold, palladium or any other conductive material. In some embodiments, the metal-rib contacts 110 and 120 may have a nonmetallic and/or nonconductive top layer. In general, individual ribs of the metal-rib contacts 110 and 120 act as terminals for the resulting device (depicted in FIGS. 3-8). To make good electrical contact to the subsequent (surface-sensitive) conductive layer, the metal-rib conductive material should not readily form an oxide barrier, or the metal-rib material forms a conductive oxide layer.

In some embodiments, each rib of metal-rib contacts 110 is of the same type of metal, and each rib of the metal-rib contacts 120 is of the same type of metal. In other embodiments, individual ribs of metal-rib contacts 110 can be different types of metal, and individual ribs of the metal-rib contacts 120 can be different types of metal.

In some embodiments, individual ribs of metal-rib contacts 110 and 120 make electrical contact with a circuit, such as a readout circuit, located at the end of or beneath respective ribs. For example, each rib of metal-rib contacts 110 and 120 may be an elongated, rod-like member or structure that extends to, or near, the edge of substrate 105 and can make electrical contact with a circuit located at the described location.

Figure 2:
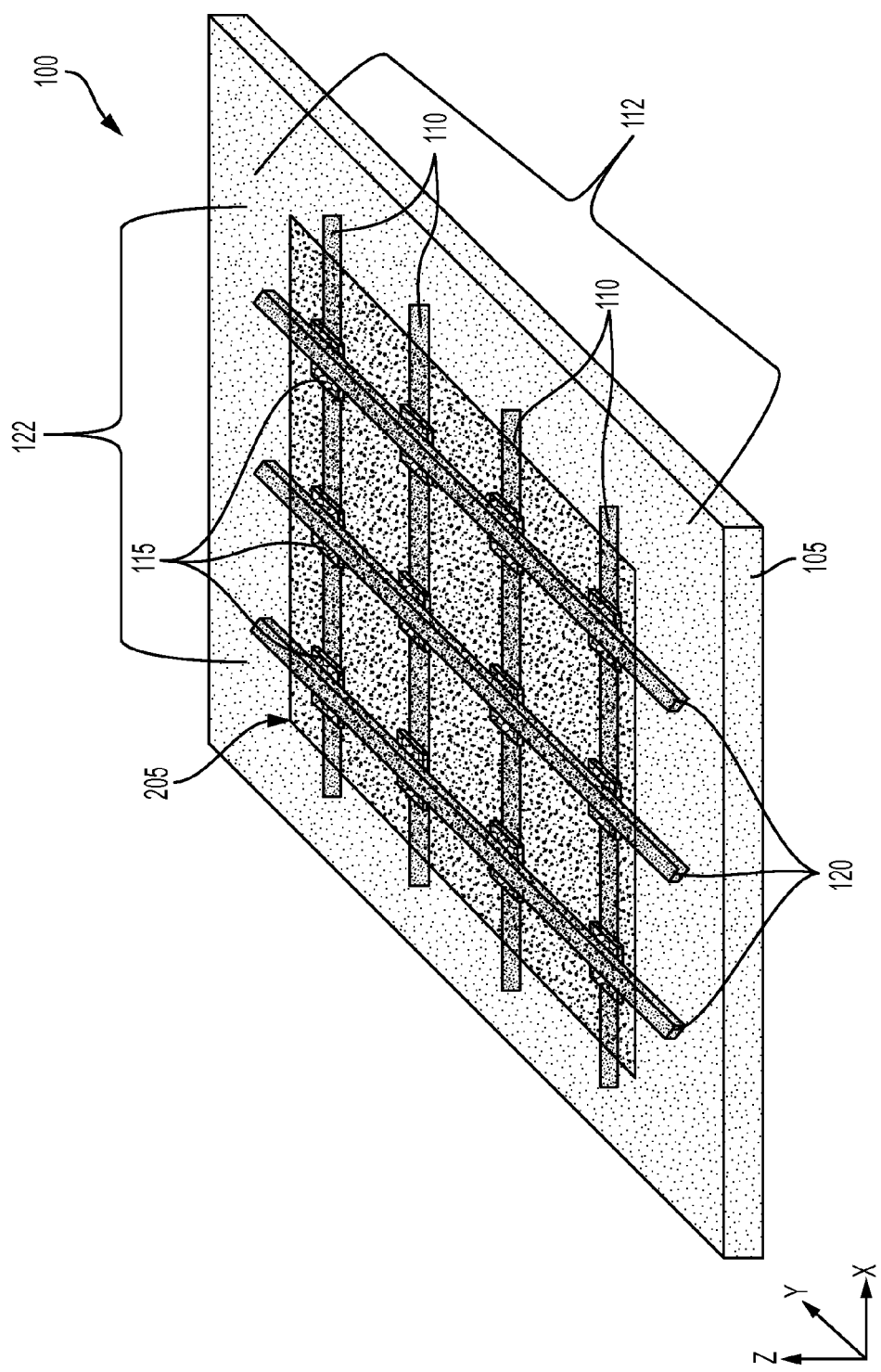
FIG. 2 is a schematic illustrating a conductive layer disposed on top of the intermediate device according to an embodiment.

FIG. 2 is a schematic of the intermediate device 100 illustrating a conductive layer 205 disposed on top of the intermediate device 100 (with a seed layer when necessary) according to an embodiment. FIG. 2 shows the active surface-sensitive conductive layer 205 as being transparent so that the elements underneath can be viewed. Also, for ease of understanding, it is noted that FIG. 2 is a simplistic view depicting the surface-sensitive conductive layer 205 as a sheet overlaying and directly touching the first and second metal-rib contacts 110 and 120. It should be appreciated that that active surface-sensitive conductive layer 205 may be conformally deposited on top of the metal-rib contacts 110 and 120, the thin insulating pads 115, and the non-conducting substrate 105, such that the surface-sensitive conductive layer 205 conforms to the shape of the elements below.

The conductive layer 205 may be deposited using a conformal deposition process, such as chemical vapor deposition (CVD), physical vapor deposition (PVD), plasma enhanced chemical vapor deposition (PECVD), atomic layer depositions (ALD), etc.

Examples of the surface-sensitive conductive layer 205 may include, e.g., topological insulators (such as $Bi_2Te_3$, $(Bi, Sb)_2Te_3$, $Bi_2Se_3$, $Bi_2Se_2Te$, $(Bi, Sb)_2Se_2Te$), a single layer or multilayer graphene, 2D semiconductors (such as $MoS_2$, $MoSe_2$), and/or a magnetic thin film. As noted above, this active conductive layer 205 is deposited on the two-dimensional metal crossbars (i.e., deposited on the first metal-rib array 112 and second metal-rib array 122).

Figure 3:
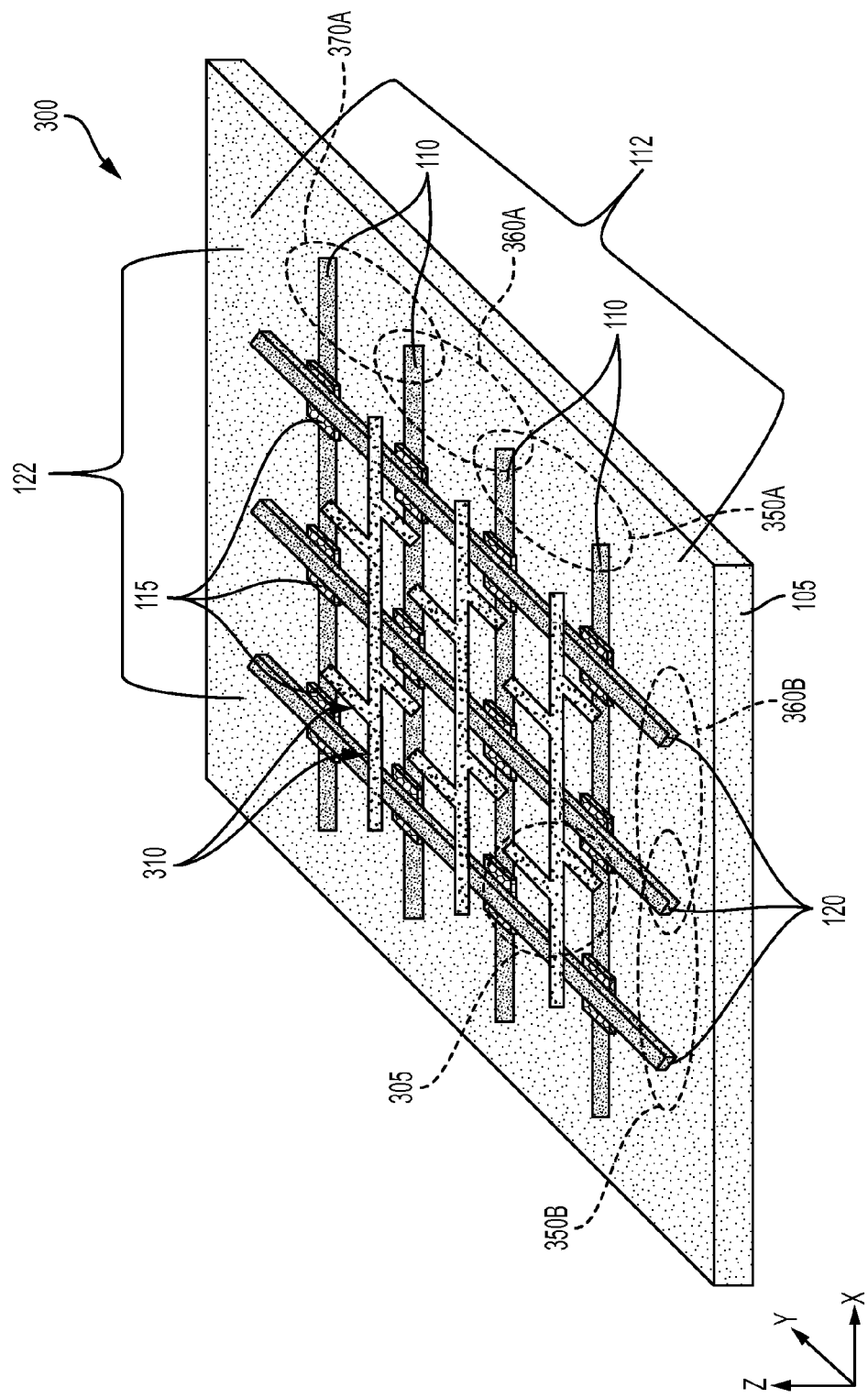
FIG. 3 is a schematic of a resultant device which is a two-dimensional array of multiple four-terminal devices according to an embodiment.

FIG. 3 is a schematic of a resultant device 300 which is a two-dimensional array of four-terminal thin film devices according to an embodiment. The surface-sensitive conductive layer 205 is etched into active surface-sensitive channels 310, which are to designate predefined active regions 305 for the four-terminal devices. The surface-sensitive conductive layer 205 (also referred to as the active channel material) has now been formed into the channels 310. Some of the active channels 310 may run along the x-axis and some run along the y-axis.

Standard lithography and etching may be utilized to form the channels 310. As one example of forming the channels 310 from the conductive layer 205, a photoresist layer may be deposited on top of the conductive layer 205 and patterned into the desired pattern of the channels 310. The exposed part of the conductive layer 205 is removed and the remaining resist is stripped-off, while the unexposed portions of the conductive layer 205 (having been protected by the photoresist) remain to thereby form the channels 310. In another example, ion beaming etching may be utilized to etch the conductive layer 205 into the pattern of the channels 310.

In embodiments, the active surface-sensitive channels 310 (i.e., etched surface-sensitive conductive layer 205) located between individual ribs of the metal-rib contacts 110 and 120 are considered active material for the resultant device 300 because these sections of the etched conductive layer 205 are in the predefined active regions 305. For example, in a four-terminal application, an electrical current can be passed across the active material (i.e., the active channels 310) acting as a channel.

According to an embedment, FIGS. 3-7 illustrate that the active region 305 may be patterned to form desirable four-terminal devices for measuring longitudinal resistance (as in magnetoresistive devices), transverse voltage (as in Hall sensors), non-local resistance (as in inverse spin-Hall devices), and/or in general Van der Pauw geometry.

FIG. 3 illustrates an example in which the resultant device 300 includes six four-terminal devices each having their own predefined active region 305. Each four-terminal device is defined by two adjacent metal-rib contacts 110, two adjacent metal-rib contacts 120, and the respective active channels 310 in the predefined active region 305 that electrically connect the two adjacent metal-rib contacts 110 and two adjacent metal-rib contacts 120. The respective channels 310 in the predefined active region 305 are surrounded by the two adjacent metal-rib contacts 110 and two adjacent metal-rib contacts 120 such that predefined active region 305 is encompassed by a square shape of the pair of adjacent metal-rib contacts 110 crossing the pair of adjacent metal-rib contacts 120 thereby defining the four-terminal device. This configuration, shown here for six devices made from three vertical and four horizontal metal-rib contact lines, is scalable and can be readily extended to incorporate any additional number of distinct device active regions through the addition of additional metal-rib contact lines.

It is noted that only one active region 305 is highlighted so as not to obscure the figure, but there are six active regions shown in FIG. 3. Particularly, FIG. 3 depicts six four-terminal devices each having its own active region 305. For example, ovals 350A and 350B designate one four-terminal device encompassing its own active region 305. As the example four-terminal device designated by 350A, 350B, a pair of the adjacent first metal-rib contacts 110 is selected by oval 350A and pair of the adjacent second metal-rib contacts 120 is selected by oval 350B. These four terminals of the first metal-rib contacts 110 (identified by oval 350A) and second metal-rib contacts 120 (identified by oval 350B) are the four-terminal device.

Any four-terminal device on the resultant device 300 can be selected/identified by selecting any pair of the adjacent first metal-rib contacts 110 (e.g., designated by either oval 350A, 360A, or 370A) and by selecting any pair of the adjacent second metal-rib contacts 120 (e.g., designated by either oval 350B or 360B). It should be appreciated that the combinations of pairs of adjacent first metal-rib contacts 110 (highlighted by oval 350A, 360A, and 370A) and adjacent second metal-rib contacts 120 (highlighted ovals 350B and 360B) results in six combinations of four-terminal devices.

FIGS. 4-7 are each examples of one four-terminal device in the two-dimensional array of four-terminal thin film devices 300. In FIGS. 4-7, the four-terminal devices are each individually depicted but in one or more embodiments, the four terminal devices 300 may be all together on the same substrate 105 as depicted in FIG. 3.

Figure 4:
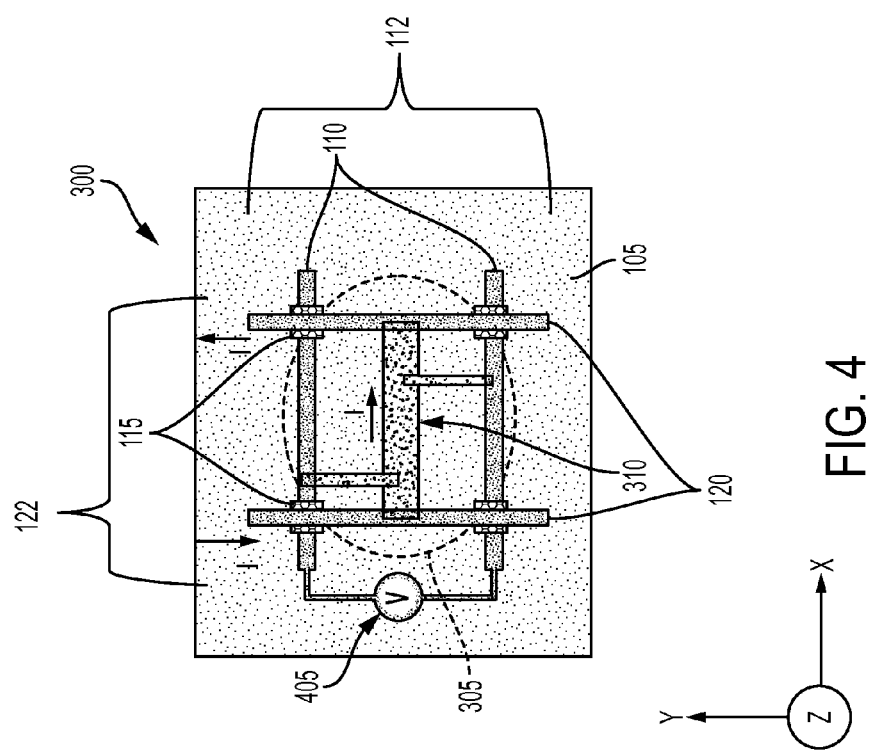
FIG. 4 is a schematic of a top-down view of the resultant device illustrating an individual four-terminal device according to an embodiment.

FIG. 4 is a schematic of a top-down view of the resultant device 300 illustrating an individual four-terminal device according to an embodiment. The two first metal-rib contacts 110 are two terminals that run horizontally in the x-axis while the two second metal-rib contacts 120 are two more terminals that run vertically in the y-axes, thereby defining four terminals of the four-terminal device. The active channels 310 connect the pair of adjacent metal-rib contacts 110 to the pair of adjacent metal-rib contacts 120. In one implementation, a voltage source (not shown) may be connected to the pair of second metal-rib contacts 120, and a voltmeter 405 may be connected to the pair of adjacent metal-rib contacts 110. Electrical current I may flow from the voltage source into the first one of the second metal-rib contacts 120 (i.e., first terminal), laterally across the active channel 310 (i.e., in the horizontal direction in the x-axes), into the second one of the second metal-rib contacts 120 (second terminal), and back to the voltage source. The voltmeter 405 is connected to the top one of the first metal-rib contacts 110 (i.e., third terminal) and to the bottom one of the first metal-rib contacts 110 (fourth terminal) in order to measure the voltage associated with electrical current I that passed through the pair of second metal-rib contacts 120. It is noted that the electrical current does not pass through the pair of first metal-rib contacts 110 in this example.

Figure 5:
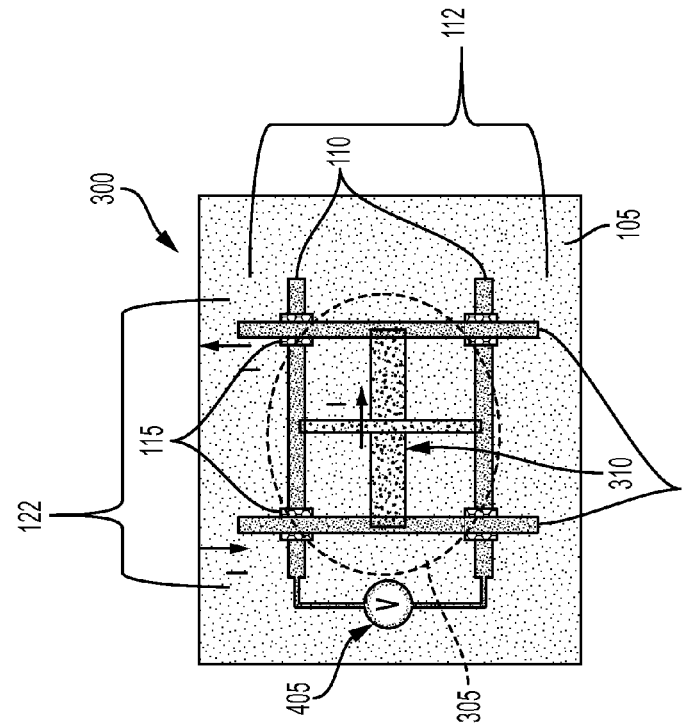
FIG. 5 is a schematic of a top-down view of the resultant device illustrating an individual four-terminal device according to an embodiment.

FIG. 5 is a schematic of a top-down view of the resultant device 300 illustrating an individual four-terminal device according to an embodiment. Just as in FIG. 4, the two first metal-rib contacts 110 are two terminals that run horizontally in the x-axis while the two second metal-rib contacts 120 are two more terminals that run vertically in the y-axes, thereby defining four terminals four-terminal device. The active channels 310 connect the pair of adjacent metal-rib contacts 110 to the pair of adjacent metal-rib contacts 120. In this case, the active channels 310 have a cross shape that electrically connect the two pair of metal-rib contacts 110 and 120. The voltage source (not shown) may be connected to the pair of second metal-rib contacts 120, and the voltmeter 405 may be connected to the pair of adjacent metal-rib contacts 110. Electrical current I may flow from the voltage source into the first one of the second metal-rib contacts 120 (i.e., first terminal), laterally across the active channel 310 (i.e., in the horizontal direction in the x-axes), into the second one of the second metal-rib contacts 120 (second terminal), and back to the voltage source. The voltmeter 405 is connected to the top one of the first metal-rib contacts 110 (i.e., third terminal) and to the bottom one of the first metal-rib contacts 110 (fourth terminal) in order to measure the voltage associated with electrical current I that passed through the pair of second metal-rib contacts 120. It is noted that the electrical current I does not pass through the pair of first metal-rib contacts 110.

Figure 6:
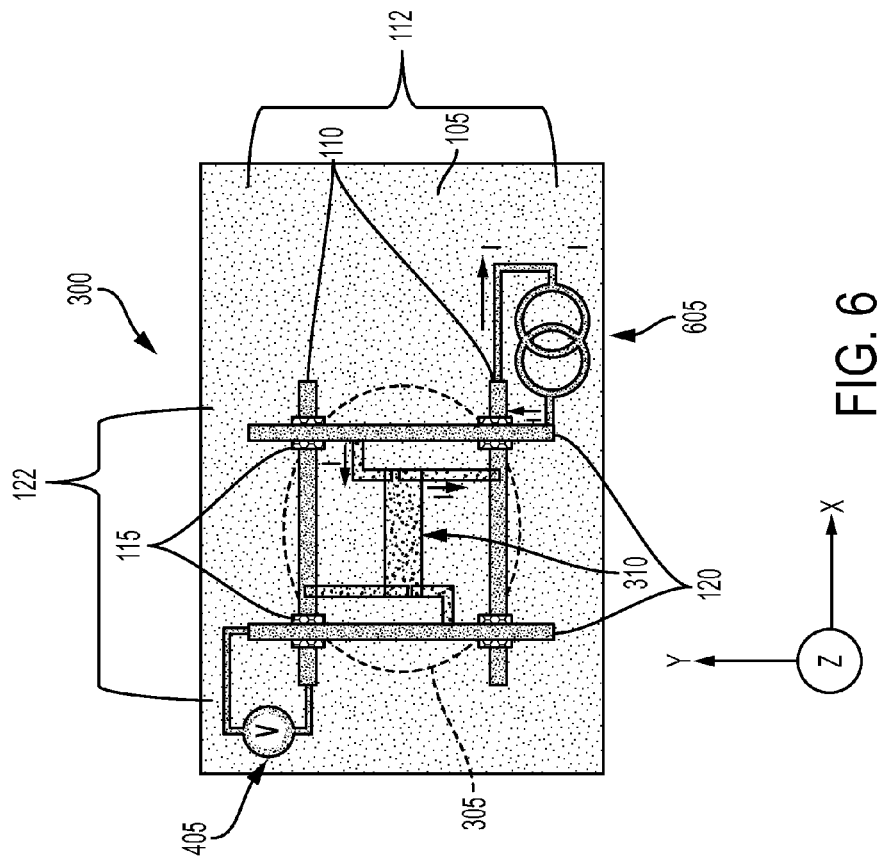
FIG. 6 is a schematic of a top-down view of the resultant device illustrating an individual four terminal device according to an embodiment.

FIG. 6 is a schematic of a top-down view of the resultant device 300 illustrating an individual four-terminal device according to an embodiment. As discussed above, the two first metal-rib contacts 110 are two terminals that run horizontally in the x-axis while the two second metal-rib contacts 120 are two more terminals that run vertically in the y-axes, thereby defining four terminals four-terminal device. The active channels 310 connect the pair of adjacent metal-rib contacts 110 to the pair of adjacent metal-rib contacts 120. In FIG. 6, the active channels 310 have a center piece with four legs respectively connected to each of the two pair of metal-rib contacts 110 and 120. Also, the four-terminal device in FIG. 6 has a current source 605 connected to the right most rib of the pair of second metal-rib contacts 120 and connected to the bottom most rib of the pair of first metal-rib contacts 110. The voltmeter 405 may be connected to the left most rib of the pair of second metal-rib contacts 120 and connected to the top most rib of the pair of first metal-rib contact 110. Electrical current I may flow from the current source 605 up into the right most rib of the second metal-rib contacts 120, left into the leg of the active channels 310 connected to the right most rib of the second metal-rib contacts 120, down through leg of the active channels 310 connected to the bottom most rib of the first metal-rib contacts 110, and right into the bottom most rib of the first metal-rib contacts 110, and back to the current source 605. The voltmeter 405 may be connected to the left most rib of the pair of second metal-rib contacts 120 and connected to the top most rib of the pair of first metal-rib contact 110 in order to measure the voltage associated with electrical current I that passed through the right most rib of the second metal-rib contacts 120, into the leg of the active channels 310 connected to the right most rib of the second metal-rib contacts 120, and down through leg of the active channels 310 connected to the bottom most rib of the first metal-rib contacts 110. In this example, electrical current did not flow into the left most rib of the pair of second metal-rib contacts 120 and the top most rib of the pair of first metal-rib contact 110 because the electrical current took the route through the active channel 310.

Figure 7:
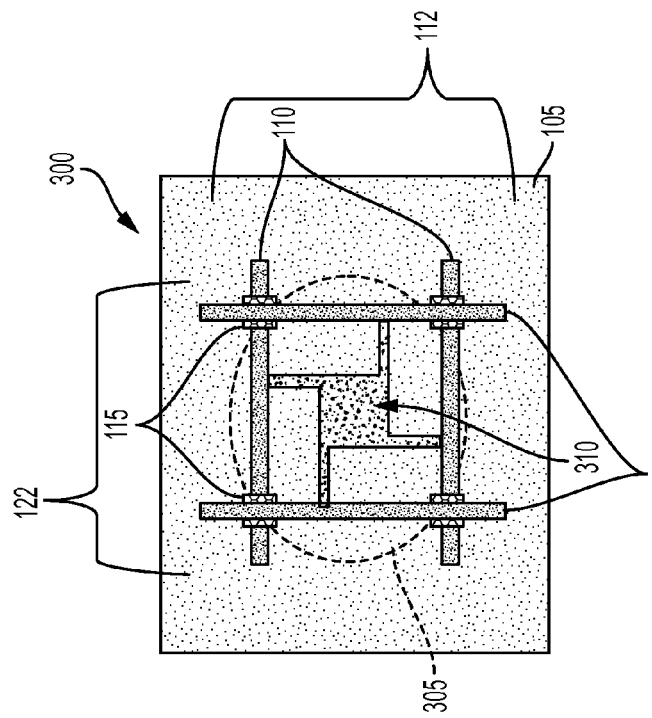
FIG. 7 is a schematic of a top-down view of the resultant device illustrating an individual four-terminal device according to an embodiment.

FIG. 7 is a schematic of a top-down view of the resultant device 300 illustrating an individual four-terminal device according to an embodiment. As discussed above, FIG. 7 includes the two first metal-rib contacts 110 as two terminals that run horizontally in the x-axis and the two second metal-rib contacts 120 as two more terminals that run vertically in the y-axes, thereby defining four terminals. However, no voltmeter, voltage source, or current source is shown although these can be connected as desired to the four-terminal device. In this case, FIG. 7 illustrates that the active surface-sensitive channels 310 may have a center rectangular (square) shape with four legs extending from the center rectangular shape such one of the four legs respectively connect to the pair of first metal-rib contacts 110 and the pair of second metal-rib contacts 120.

In FIG. 3 where six four-terminal devices as shown, measurements of a specific four-terminal device in the two-dimensional array is performed by passing current through two metal-rib contacts surrounding the specific four-terminal device under test and reading voltage across the other two metal-rib contacts (as depicted in FIGS. 4-7). Sequential single-channel detection of the two-dimensional array elements can be accomplished using an external switch matrix. It should be appreciated that multi-channel detection of the two-dimensional array elements may be accomplished using multiplexing methods known in the art, such as frequency division multiplexing, time division multiplexing, etc.

Figure 8:
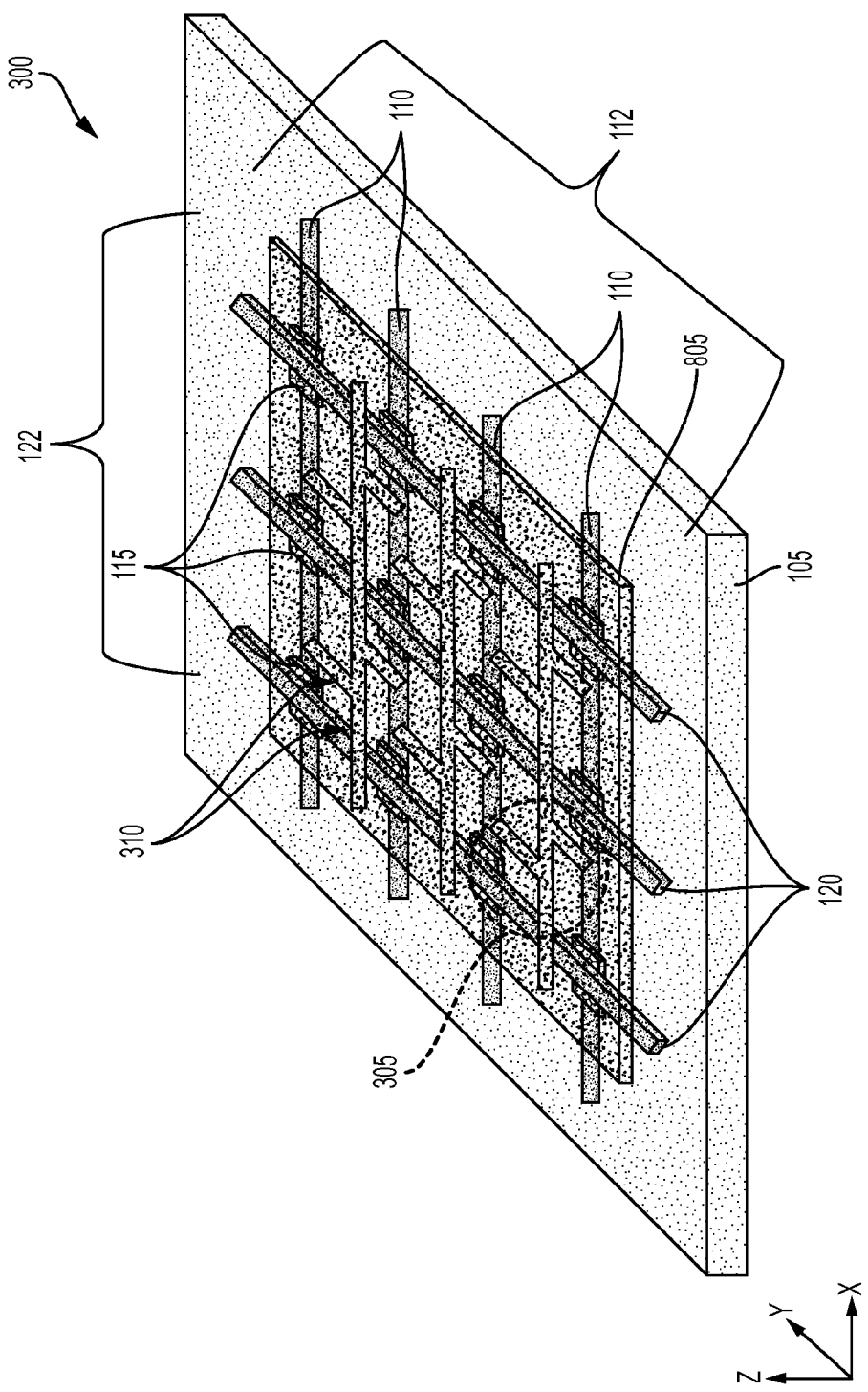
FIG. 8 is a schematic of the resultant device illustrating the four-terminal devices of the two-dimensional array structure encapsulated by a cap layer according to an embodiment.

According to an embodiment, FIG. 8 is a schematic of the resultant device 300 illustrating the four-terminal devices in the two-dimensional array structure encapsulated by non-conformal or semi-conformal deposition of a cap layer 805 (which is a protective layer). In one embodiment, the resultant device 300 may be encapsulated either in vacuum or inert gas. Prior to device encapsulation, in-situ post-lithography processing is performed to restore the surface of the active regions 305, such as thermal annealing of graphene and vacuum de-capping of topological insulators.

Figure 9:
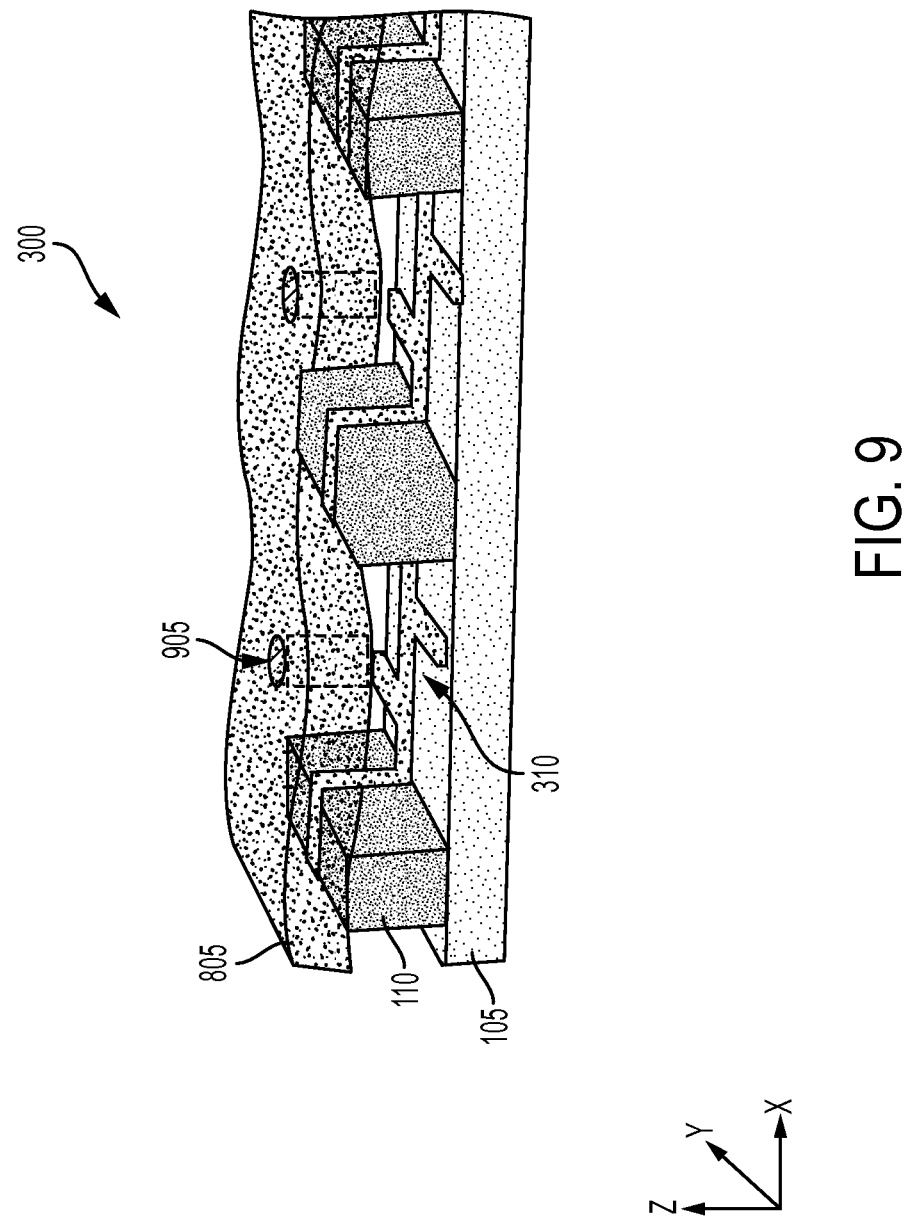
FIG. 9 is a cross-sectional view of the resultant device illustrating conductive channels extending along the substrate and side walls of the metal-rib contacts according to an embodiment.
Figure 10:
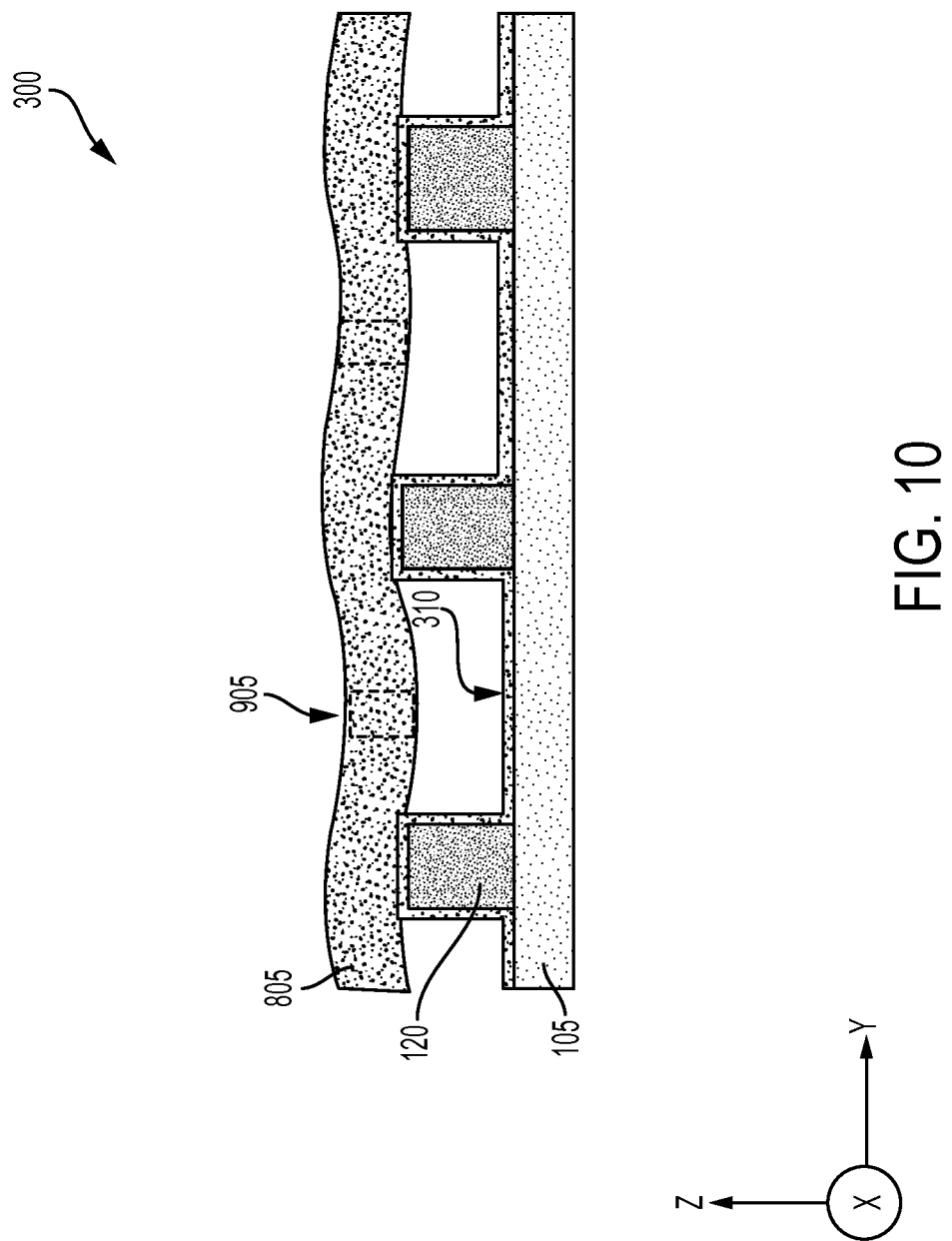
FIG. 10 is a cross-sectional view of the resultant device illustrating conductive channels extending along the substrate and on the metal-rib contacts according to an embodiment.

The cap layer 805 may be a dielectric layer. Examples of the cap layer 805 may include $SiN_x$, $SiO_x$, h-BN (hexagonal one boron nitride). FIG. 9 is a cross-sectional view of the resultant device 300 illustrating how the surface-sensitive channels 310 (etched surface-sensitive conductive layer 205) run along the substrate 105 and up the side walls of the first metal-rib contacts 110 (and similarly run up the sidewalls of the second metal-rib contacts 120 not shown). FIG. 10 is a cross-sectional view of the resultant device 300 illustrating how the surface-sensitive channels 310 (etched conductive layer 205) run on top of the as well as up the side walls of the first metal-rib contacts 110 (and similarly on top of the second metal-rib contacts 110 not shown).

In one embodiment of the resultant device 300 (array structure), the semi-conformal or non-conformal dielectric caps 805 may have openings 905 for exposing the sensing devices to chemical agents for chemical sensing applications. For example, the openings 905 through the dielectric cap layer 805 are illustrated in FIGS. 9 and 10. However, in another embodiment, the openings 905 may not be present.

Figure 11:
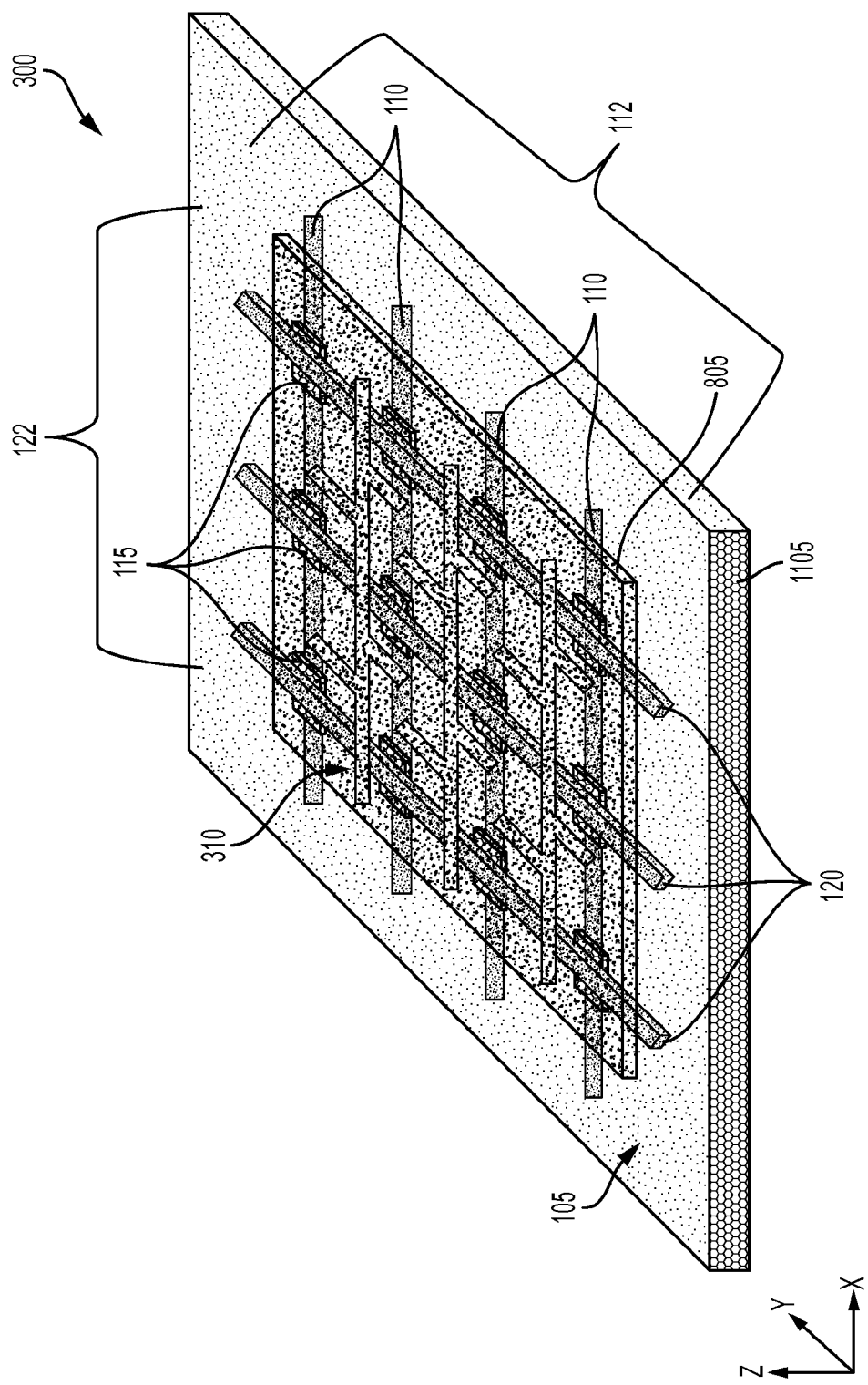
FIG. 11 is a schematic of the resultant device illustrating the four-terminal devices of the two-dimensional array structure with a global back gate according to an embodiment.

FIG. 11 is a schematic of the resultant device 300 illustrating the four-terminal devices of the two-dimensional array structure with a back gate 1105 according to an embodiment. In this embodiment, the substrate 105 comprises an insulating dielectric layer, such as e.g., SiOx, SiNx, and/or h-BN. The substrate 105 is disposed on a conducting bulk as the back gate 1105 to enable global back-gating of the individual four terminal devices. The material of the back gate 1105 may include, e.g., highly doped silicon, etc., such that the back gate 1105 is conducting. A voltage source may be applied to the back gate 1105 to change the properties of the four-terminal devices on the front.

In FIG. 11, a global back gate 1105 is shown. However, in another embodiment, an individual back gate (e.g., six individual back gates) may be formed underneath the active region 305 for each of the four-terminal devices. Instead of having to dope the bulk material of the back gate 1105, only six isolated regions (corresponding to the six active regions 305) are doped in the back gate 1105.

In another embodiment, the resultant device 300 may have metal crossbars (which are the crossing first metal-rib contacts 110 and second metal-rib contacts 120) that comprise different types of metals in periodic or aperiodic fashion to create n-type or p-type devices by harnessing the work function differences between the metal contacts and the active materials.

In yet another embodiment, the resultant device 300 may include on-chip switches. The on-chip switches are built onto the two-dimensional array using embedded local gates to open/close the band gap of a graphene multilayer or modulate the potential of a two-dimensional semiconductor channel, turning off/on the sensing devices.

Figure 12:
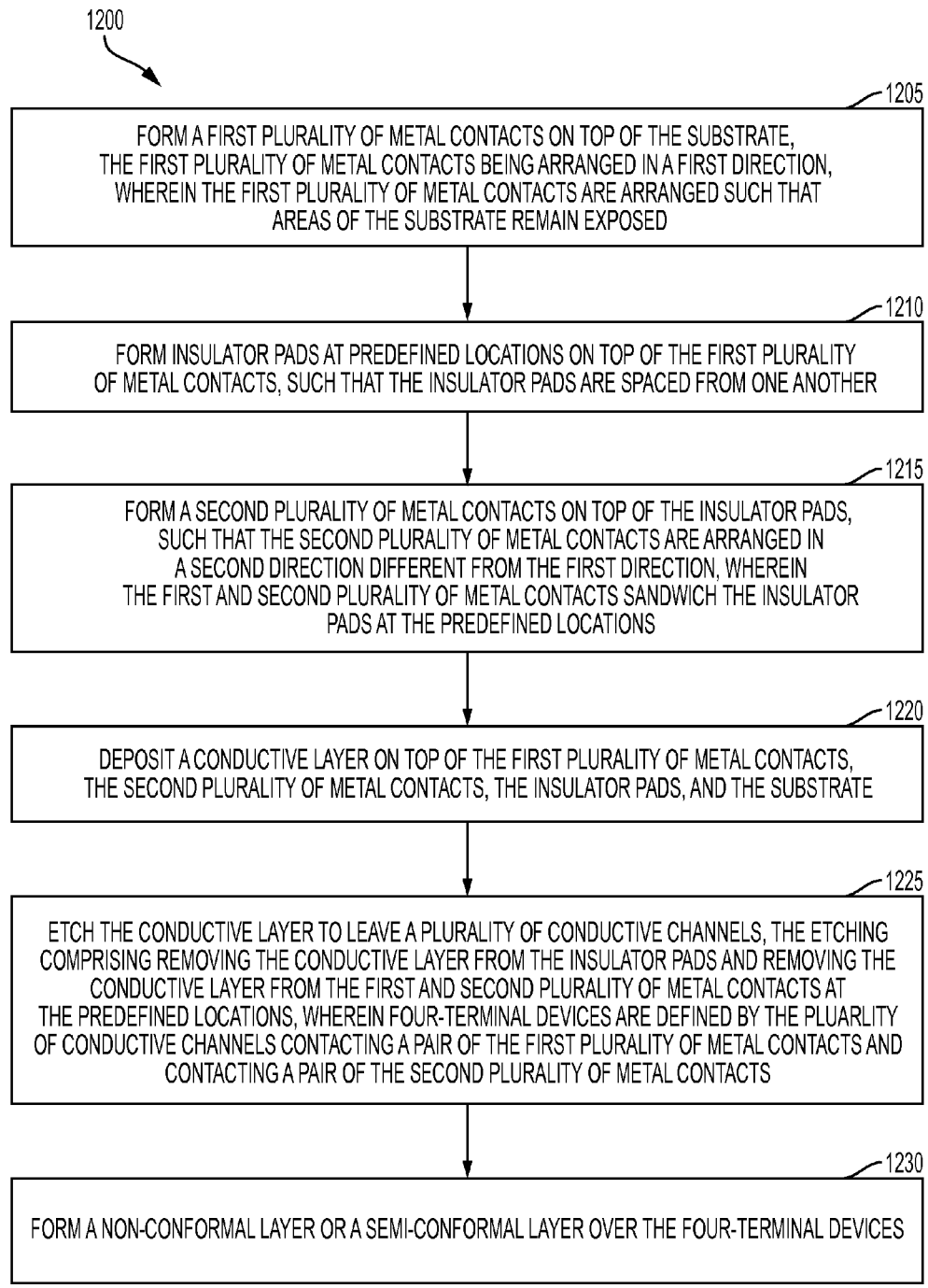
FIG. 12 is a flow chart of a method of fabricating a two-dimensional array structure with four-terminal devices according to an embodiment.

FIG. 12 is a flow chart 1200 of a method of fabricating a semiconductor device 300 (i.e., two-dimensional array structure with four-terminal devices) according to an embodiment.

At block 1205, a first plurality of metal contacts 110 formed on top of the substrate 105, in which the first plurality of metal contacts 110 are arranged in a first direction (e.g., along the x-axes), where the first plurality of metal contacts 110 are arranged such that areas of the substrate 105 remain exposed.

At block 1210, insulator pads 115 are formed at predefined locations on top of the first plurality of metal contacts 110, such that the insulator pads 115 are spaced from one another.

At block 1215, a second plurality of metal contacts 120 formed on top of the insulator pads 115, such that the second plurality of metal contacts 120 are arranged in a second direction (e.g., along the y-axes) different from the first direction, where the first and second plurality of metal contacts sandwich the insulator pads 115 at the predefined locations. The predefined locations are where the insulator pads 115 are to be formed and where the second plurality of metal contacts 120 intersect the first plurality of metal contacts 110.

At block 1220, a conductive layer 205 is formed on top of the first plurality of metal contacts 110, the second plurality of metal contacts 120, the insulator pads 115, and the substrate 105.

At block 1225, the conductive layer 205 is etched to leave a plurality of surface-sensitive conductive channels 310, in which the etching comprises removing the conductive layer 205 from the insulator pads 115 and removing the conductive layer 205 from the first and second plurality of metal contacts 110, 120 at the predefined locations, where four-terminal devices are defined by the plurality of surface-sensitive conductive channels 310 contacting a pair of the first plurality of metal contacts and contacting a pair of the second plurality of metal contacts.

At block 1230, a non-conformal protective layer or a semi-conformal protective layer (e.g., cap layer 805) may be formed over the four-terminal devices, as depicted in FIGS. 8-10. The cap layer 805 may comprise one or more opening 905 for chemical sensing in the active region 305.

The pair of the first plurality of metal contacts 110 are adjacent to one another (such as highlighted ovals 350A, 360A, 370A), and the pair of the second plurality of metal contacts 120 are adjacent to one another (such as highlighted ovals 350B, 360B).

An active region 305 for each of the four-terminal devices is defined by the plurality of surface-sensitive conductive channels 310 contacting the pair of the first plurality of metal contacts 110 and contacting the pair of the second plurality of metal contacts 120.

The plurality of surface-sensitive conductive channels 310 in the active region 305 are resistive sensing elements for the four-terminal devices, as depicted in FIG. 4, and the plurality of surface-sensitive conductive channels are encapsulated in a vacuum or inert gas, as depicted in FIGS. 8, 9, and 10 (without holes 905).

The plurality of surface-sensitive conductive channels 310 in the active region 305 are Hall voltage sensing elements for the four-terminal devices, as depicted in FIG. 5, and the plurality of surface-sensitive conductive channels 310 are encapsulated in a vacuum or inert gas, as depicted in FIGS. 8, 9, and 10 (without holes 905).

Further, the surface-sensitive plurality of conductive channels 310 in the active region 305 are nonlocal voltage sensing elements for the four-terminal devices, as depicted in FIG. 6, and the plurality of surface-sensitive conductive channels 310 are encapsulated in a vacuum or inert gas, as depicted in FIGS. 8, 9, and 10 (without holes 905).

In one implementation, each of the four-terminal devices has a global back gate 1105 formed on an opposite side of the substrate 105, as depicted in FIG. 11.

The first plurality of metal contacts 110 has a different metal than the second plurality of metal contacts 120.

The first plurality of metal contacts 110 and the second plurality of metal contacts 120 form a two-dimensional array, and the two-dimensional array comprises the four-terminal devices.

It will be noted that various microelectronic device fabrication methods may be utilized to fabricate the components/elements discussed herein as understood by one skilled in the art. In semiconductor device fabrication, the various processing steps fall into four general categories: deposition, removal, patterning, and modification of electrical properties.

Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others.

Removal is any process that removes material from the wafer: examples include etch processes (either wet or dry), and chemical-mechanical planarization (CMP), etc.

Patterning is the shaping or altering of deposited materials, and is generally referred to as lithography. For example, in conventional lithography, the wafer is coated with a chemical called a photoresist; then, a machine called a stepper focuses, aligns, and moves a mask, exposing select portions of the wafer below to short wavelength light; the exposed regions are washed away by a developer solution. After etching or other processing, the remaining photoresist is removed. Patterning also includes electron-beam lithography.

Modification of electrical properties may include doping, such as doping transistor sources and drains, generally by diffusion and/or by ion implantation. These doping processes are followed by furnace annealing or by rapid thermal annealing (RTA). Annealing serves to activate the implanted dopants.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of fabricating a semiconductor device, the method comprising:
 forming first metal contacts on top of a substrate, the first metal contacts being arranged in a first direction, wherein the first metal contacts are arranged such that areas of the substrate remain exposed;
 forming insulator pads at predefined locations on top of the first metal contacts, such that the insulator pads are spaced from one another;
 forming second metal contacts on top of the insulator pads, such that the second metal contacts are arranged in a second direction different from the first direction, wherein the first and second metal contacts sandwich the insulator pads at the predefined locations;
 depositing a surface-sensitive conductive layer on top of the first plurality of metal contacts, the second plurality of metal contacts, the insulator pads, and the substrate; and
 etching the surface-sensitive conductive layer to leave conductive channels, the etching including removing the surface-sensitive conductive layer from the insulator pads and removing the surface-sensitive conductive layer from the first and second metal contacts at the predefined locations to form four-terminal devices, wherein each of the four-terminal devices is defined by a conductive channel contacting a pair of the first metal contacts and contacting a pair of the second metal contacts;
 wherein the surface-sensitive conductive layer includes at least one of:
  topological insulators having Bi and at least one of Te, Sb, and Se;
  material including graphene;
  material including MoS or MoSe; and
  a magnetic film.

2. The method of claim 1, wherein the pair of the first metal contacts are adjacent to one another; and
 wherein the pair of the second metal contacts are adjacent to one another.

3. The method of claim 2, wherein an active region for each of the four-terminal devices is defined by the conductive channels contacting the pair of the first metal contacts and contacting the pair of the second metal contacts.

4. The method of claim 3, wherein the conductive channels in the active region are resistive sensing elements for the four-terminal devices; and
 wherein the conductive channels are encapsulated in a vacuum or inert gas.

5. The method of claim 3, wherein the conductive channels in the active region are Hall voltage sensing elements for the four-terminal devices; and
 wherein the conductive channels are encapsulated in a vacuum or inert gas.

6. The method of claim 3, wherein the conductive channels in the active region are nonlocal voltage sensing elements for the four-terminal devices; and
 wherein the conductive channels are encapsulated in a vacuum or inert gas.

7. The method of claim 3, wherein a cap layer is formed over the four-terminal devices;
 wherein the cap layer comprises one or more opening for chemical sensing in the active region.

8. The method of claim 1, wherein each of the four-terminal devices has a back gate formed on an opposite side of the substrate.

9. The method of claim 1, wherein the first metal contacts have a different metal than the second metal contacts.

10. The method of claim 1, wherein the first metal contacts and the second metal contacts form a two-dimensional array; and
 wherein the two-dimensional array comprises the four-terminal devices.

* * * * *